United States Patent
Sakuragi

(10) Patent No.: US 11,464,571 B2
(45) Date of Patent: *Oct. 11, 2022

(54) VIRTUAL STENT PLACEMENT APPARATUS, VIRTUAL STENT PLACEMENT METHOD, AND VIRTUAL STENT PLACEMENT PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 380 days.

This patent is subject to a terminal disclaimer.

(21) Appl. No.: 16/783,135

(22) Filed: Feb. 5, 2020

(65) Prior Publication Data

US 2020/0188027 A1    Jun. 18, 2020

Related U.S. Application Data

(63) Continuation of application No. PCT/JP2018/025698, filed on Jul. 6, 2018.

(30) Foreign Application Priority Data

Sep. 27, 2017   (JP) .............................. JP2017-185647

(51) Int. Cl.
  *A61B 34/10*    (2016.01)
  *G06T 7/00*    (2017.01)
  *G06V 10/44*    (2022.01)

(52) U.S. Cl.
  CPC ............ *A61B 34/10* (2016.02); *G06T 7/0012* (2013.01); *G06V 10/44* (2022.01);
  (Continued)

(58) Field of Classification Search
  CPC ........ A61B 2034/102; A61B 2034/105; A61B 2034/107; G06T 2207/10081;
  (Continued)

(56) References Cited

U.S. PATENT DOCUMENTS

2002/0068968 A1    6/2002  Hupp
2007/0135707 A1    6/2007  Redel et al.
(Continued)

FOREIGN PATENT DOCUMENTS

| JP | 2001079097 | 3/2001 |
|----|------------|--------|
| JP | 2003245360 | 9/2003 |
| WO | 2012170448 | 12/2012 |

OTHER PUBLICATIONS

Machine translation, JP2001079097 published on Mar. 27, 2001. (Year: 2001).*

(Continued)

*Primary Examiner* — Sing-Wai Wu
(74) *Attorney, Agent, or Firm* — JCIPRNET

(57) ABSTRACT

Provided are a virtual stent placement apparatus, a virtual stent placement method, and a virtual stent placement program that simplify an operation of virtually placing a stent in a blood vessel extracted from a medical image. An extraction unit (22) extracts a blood vessel region (30) from a three-dimensional image (V0). A display control unit (26) displays a three-dimensional image (V1) including the blood vessel region (30). The information acquisition unit (23) acquires information of the diameter of a virtual stent placed in the blood vessel region (30), a maximum contour length of the virtual stent, and a start position (S1) in a case in which the virtual stent is placed. A placement unit (24) places the virtual stent having a maximum contour length (L0) from the start position (S1) along a maximum contour line of the blood vessel region (30) in the blood vessel region (30).

9 Claims, 10 Drawing Sheets

(52) U.S. Cl.
CPC ... *A61B 2034/102* (2016.02); *A61B 2034/105* (2016.02); *A61B 2034/107* (2016.02); *G06T 2207/10081* (2013.01); *G06T 2207/20116* (2013.01); *G06T 2207/30101* (2013.01)

(58) Field of Classification Search
CPC . G06T 2207/20116; G06T 2207/30101; G06T 7/0012; G06V 10/44
See application file for complete search history.

(56) References Cited

U.S. PATENT DOCUMENTS

| | | | |
|---|---|---|---|
| 2008/0177368 A1* | 7/2008 | Goto | A61F 2/95 623/1.11 |
| 2009/0088830 A1* | 4/2009 | Mohamed | A61B 6/4423 623/1.11 |
| 2010/0094401 A1 | 4/2010 | Kolbel et al. | |
| 2016/0232659 A1 | 8/2016 | Larrabide | |

OTHER PUBLICATIONS

"International Search Report (Form PCT/ISA/210) of PCT/JP2018/025698," dated Sep. 25, 2018, with English translation thereof, pp. 1-5.

"Written Opinion of the International Searching Authority (Form PCT/ISA/237) of PCT/JP2018/025698," dated Sep. 25, 2018, with English translation thereof, pp. 1-7.

* cited by examiner

VIRTUAL STENT PLACEMENT APPARATUS, VIRTUAL STENT PLACEMENT METHOD, AND VIRTUAL STENT PLACEMENT PROGRAM

CROSS-REFERENCE TO RELATED APPLICATIONS

This application is a Continuation of PCT International Application No. PCT/JP2018/025698 filed on Jul. 6, 2018, which claims priority under 35 U.S.C § 119(a) to Japanese Patent Application No. 2017-185647 filed on Sep. 27, 2017. Each of the above application(s) is hereby expressly incorporated by reference, in its entirety, into the present application.

BACKGROUND OF THE INVENTION

1. Field of the Invention

The present invention relates to a virtual stent placement apparatus, a virtual stent placement method, and a virtual stent placement program for placing a virtual stent in a blood vessel region extracted from a medical image such as a computed radiography (CT) image.

2. Description of the Related Art

In recent years, as a treatment for an aneurysm or the like, a surgical operation has been performed which places a stent in the artery. In addition, before a surgical operation, an artery region is extracted from a medical image, such as a CT image of a patient, and a simulation in which a stent is virtually placed in the extracted artery region is performed to check the size of the stent to be actually placed in advance.

In order to virtually place a stent, generally, a core line of the blood vessel is extracted from the blood vessel, such the extracted artery, and a virtual stent having a specific length is placed along the core line. However, in an extremely curved blood vessel, such as an aortic arch, for example, the length of the outer side (that is, the large curvature side) of the curvature of the blood vessel is larger than the length of the core line. In a case in which the virtual stent is placed in the curved blood vessel on the basis of the core line and the size of the stent is determined, there is a problem that the length of the stent on the large curvature side of the blood vessel is insufficient in the actual placement of the stent in the patient.

Therefore, the maximum contour length of the large curvature side of the virtual stent is calculated (see JP2001-079097A). The technique described in JP2001-079097A extracts a blood vessel from a CT image, generates a stent graft model on the basis of a core line of the blood vessel and a plurality of rings perpendicular to the core line, and designs a stent. In this case, the maximum contour length of the large curvature side of the virtual stent is calculated by setting the interval at which the rings are placed, the number of rings, and the radius of the rings.

The use of the technique described in JP2001-079097A makes it possible to know the maximum contour length of the stent in advance. Therefore, in a case in which the stent is actually placed in the patient, it is possible to solve the problem that the length of the stent is insufficient on the large curvature side of the blood vessel.

SUMMARY OF THE INVENTION

However, in the method disclosed in JP2001-079097A, it is difficult to calculate the maximum contour length of the stent unless the stent is virtually placed. For this reason, in a case in which the method described in JP2001-079097A is used, it is necessary to repeat the placement of the stent and the calculation of the maximum contour length until the stent with a desired size is determined. As a result, the operation of placing the virtual stent becomes complicated.

The invention has been made in view of the above-mentioned problems and an object of the invention is to provide a technique that simplifies an operation in a case in which a stent is virtually placed in the blood vessel extracted from a medical image.

According to the invention, there is provided a virtual stent placement apparatus comprising: an extraction unit that extracts a blood vessel region from a medical image; an information acquisition unit that acquires information of a diameter of a virtual stent which is placed in the blood vessel region, a maximum contour length of the virtual stent, and a start position in a case in which the virtual stent is placed; and a placement unit that places the virtual stent having the maximum contour length from the start position along a maximum contour line of the blood vessel region in the blood vessel region.

In the virtual stent placement apparatus according to the invention, the placement unit may set an end position of the virtual stent on the basis of a position of the maximum contour length.

In the virtual stent placement apparatus according to the invention, the information acquisition unit may estimate the diameter of the virtual stent from the blood vessel region.

In the virtual stent placement apparatus according to the invention, the extraction unit may further extract a core line of the blood vessel region from the medical image. The virtual stent placement apparatus may further comprise an inclination change unit that changes an inclination of stent cross sections which are cross sections of the placed virtual stent at the start position and the end position with respect to cross sections perpendicular to the core line.

In the virtual stent placement apparatus according to the invention, the inclination change unit may receive a command to change the inclination of the stent cross section and change the inclination of the stent cross section with respect to the cross section perpendicular to the core line.

In the virtual stent placement apparatus according to the invention, the inclination change unit may change the inclination of the stent cross section with respect to the cross section perpendicular to the core line to avoid an overlap between the stent cross section and a branch of the blood vessel region.

In the virtual stent placement apparatus according to the invention, the inclination change unit may bring the stent cross section into contact with a contour line of the blood vessel region having a maximum contour length to change the inclination of the stent cross section.

In the virtual stent placement apparatus according to the invention, the placement unit may change a position where the virtual stent is placed with the change in the inclination of the stent cross section.

According to the invention, there is provided a virtual stent placement method comprising: extracting a blood vessel region from a medical image; acquiring information of a diameter of a virtual stent which is placed in the blood vessel region, a maximum contour length of the virtual stent, and a start position in a case in which the virtual stent is placed; and placing the virtual stent having the maximum contour length from the start position along a maximum contour line of the blood vessel region in the blood vessel region.

In addition, a program that causes a computer to perform the virtual stent placement method according to the invention may be provided.

According to the invention, there is provided another virtual stent placement apparatus comprising a memory that stores commands to be executed by a computer and a processor that is configured to execute the stored commands. The processor performs a process of extracting a blood vessel region from a medical image, a process of acquiring information of a diameter of a virtual stent which is placed in the blood vessel region, a maximum contour length of the virtual stent, and a start position in a case in which the virtual stent is placed, and a process of placing the virtual stent having the maximum contour length from the start position along a maximum contour line of the blood vessel region in the blood vessel region.

According to the invention, a blood vessel region is extracted from a medical image and the information of a diameter of a virtual stent which is placed in the blood vessel region, a maximum contour length of the virtual stent, and a start position in a case in which the virtual stent is placed is acquired. Then, the virtual stent having the maximum contour length from the start position along a maximum contour line of the blood vessel region is placed in the blood vessel region. Therefore, it is not necessary to repeat the placement of the stent and the setting of the maximum contour length until the stent with a desired size is determined. As a result, it is possible to simplify the operation of placing the virtual stent.

DESCRIPTION OF THE PREFERRED EMBODIMENTS

Figure 1:
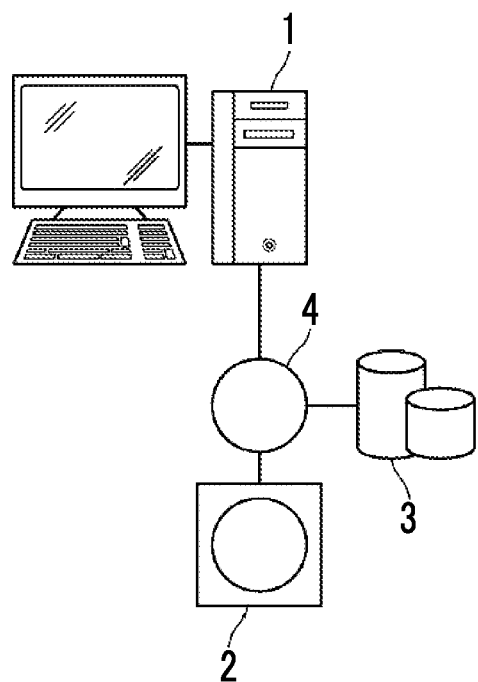
FIG. 1 is a hardware configuration diagram illustrating the outline of a diagnosis support system to which a virtual stent placement apparatus according to an embodiment of the invention is applied.

Hereinafter, an embodiment of the invention will be described with reference to the drawings. FIG. 1 is a hardware configuration diagram illustrating the outline of a diagnosis support system to which a virtual stent placement apparatus according to the embodiment of the invention is applied. As illustrated in FIG. 1, in the diagnosis support system, a virtual stent placement apparatus 1 according to this embodiment, a three-dimensional imaging apparatus 2, and an image storage server 3 are connected through a network 4 so as to communicate with each other. In the diagnosis support system, a three-dimensional image of the aorta of a subject is displayed and a virtual stent is placed in the aorta included in the displayed three-dimensional image as a simulation for correctly placing the stent in the aorta.

The three-dimensional imaging apparatus 2 is an apparatus that captures an image of a diagnosis target part of the subject and generates a three-dimensional image indicating the part. Specifically, the three-dimensional imaging apparatus 2 is, for example, a CT apparatus, a magnetic resonance imaging (MRI) apparatus, or a positron emission tomography (PET) apparatus. A three-dimensional image V0 generated by the three-dimensional imaging apparatus 2 is transmitted to the image storage server 3 and is then stored therein. In this embodiment, since the place in which the virtual stent is placed is the aorta of the subject, the diagnosis target part of the subject is the chest including the aorta. The three-dimensional imaging apparatus 2 is a CT apparatus and generates a three-dimensional image formed by tomographic images of a plurality of axial cross sections for the chest of the subject. The three-dimensional image corresponds to a medical image.

The image storage server 3 is a computer that stores various kinds of data and manages the data and comprises a large-capacity external storage device and database management software. The image storage server 3 communicates with other apparatuses through the wired or wireless network 4 to transmit and receive, for example, image data. Specifically, the image storage server 3 acquires image data, such as the three-dimensional image generated by the three-dimensional imaging apparatus 2, through the network 4, stores the image data in a recording medium, such as a large-capacity external storage device, and manages the image data. The storage format of the image data and the communication between the apparatuses through the network 4 are based on a protocol such as Digital Imaging and Communication in Medicine (DICOM).

The virtual stent placement apparatus 1 is configured by installing a virtual stent placement program according to the invention in one computer. The computer may be a workstation or a personal computer that is directly operated by a doctor who performs diagnosis or may be a server computer that is connected to the computer through the network. An image display program is recorded on a recording medium, such as a digital versatile disc (DVD) or a compact disc read only memory (CD-ROM), is distributed, and is then installed in the computer from the recording medium. Alternatively, the image display program is stored in a storage device of a server computer connected to the network or a network storage such that it can be accessed from the outside, is downloaded to the computer used by the doctor on demand, and is then installed in the computer.

Figure 2:
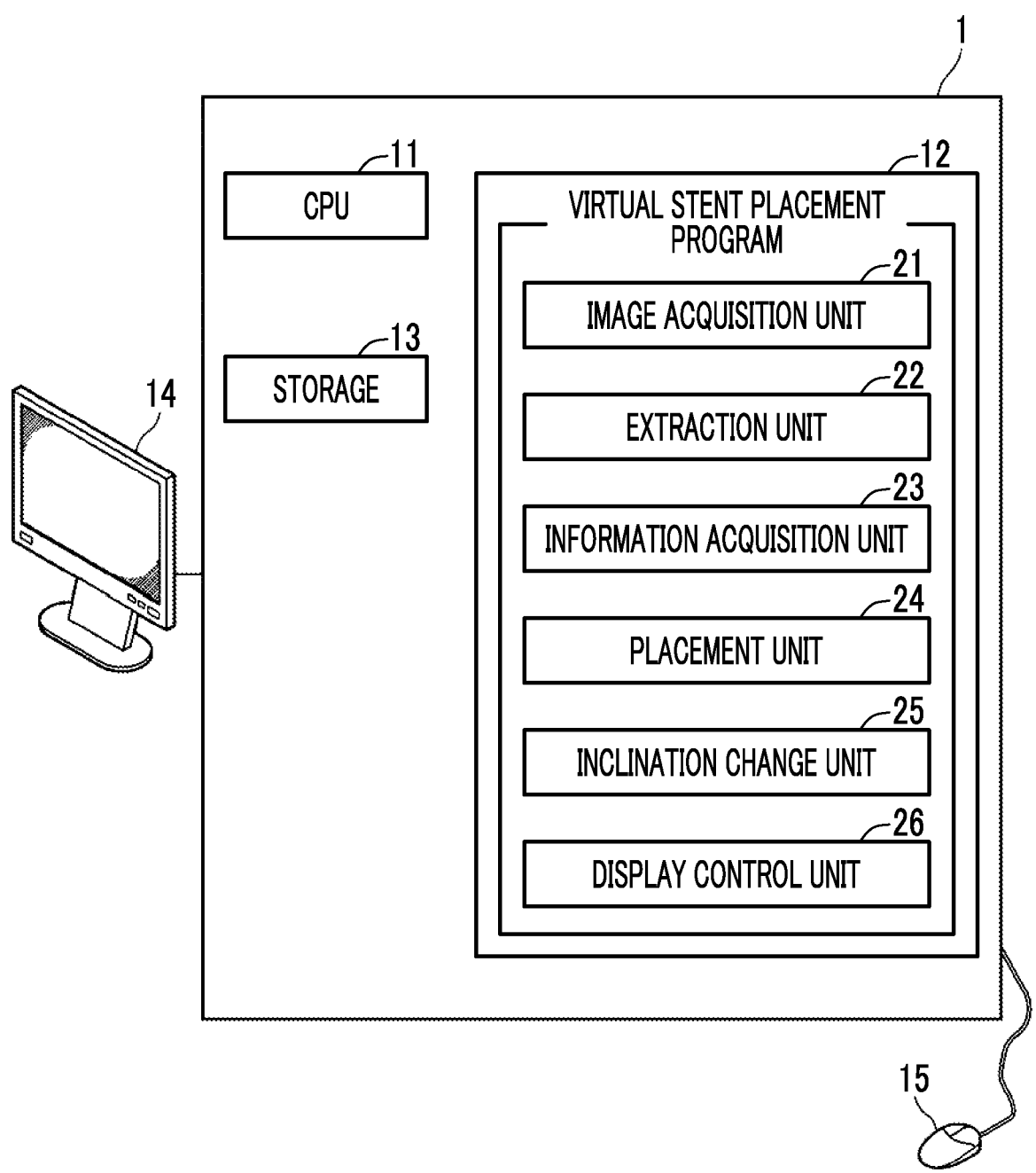
FIG. 2 is a diagram schematically illustrating the configuration of the virtual stent placement apparatus according to the embodiment of the invention.

FIG. 2 is a diagram schematically illustrating the configuration of the virtual stent placement apparatus 1 according to this embodiment implemented by installing the virtual stent placement program in the computer. As illustrated in FIG. 2, the virtual stent placement apparatus 1 comprises a central processing unit (CPU) 11, a memory 12, and a storage 13 as the configuration of a standard workstation. In addition, a display 14, such as a liquid crystal display, and an input unit 15, such as a mouse or a keyboard, are connected to the virtual stent placement apparatus 1.

The storage 13 is a storage device such as a hard disk drive or a solid state drive (SSD). The storage 13 stores various kinds of information including the three-dimensional image V0 of the subject acquired from the image storage server 3 through the network 4 and information required for processes.

The memory 12 stores the virtual stent placement program. The virtual stent placement program defines, as the processes performed by the CPU 11, an image acquisition process that acquires the three-dimensional image V0, an extraction process that extracts a blood vessel region from the three-dimensional image V0, an information acquisition process that acquires information of the diameter of the virtual stent placed in the blood vessel region, a maximum contour length of the virtual stent, and a start position in a case in which the virtual stent is placed, a placement process that places the virtual stent having the maximum contour length from the start position along a maximum contour line of the blood vessel region in the blood vessel region, an inclination change process that changes the inclination of stent cross sections which are the cross sections of the placed virtual stent at the start position and an end position with respect to cross sections perpendicular to a core line, and a display control process that displays, for example, the three-dimensional image V0.

The CPU 11 performs these processes according to the program such that the computer functions as an image acquisition unit 21, an extraction unit 22, an information acquisition unit 23, a placement unit 24, an inclination change unit 25, and a display control unit 26. In this embodiment, the functions of each unit are implemented by the virtual stent placement program. However, the invention is not limited thereto. For example, a plurality of integrated circuits (IC), a processor, an application specific integrated circuit (ASIC), a field-programmable gate array (FPGA), and a memory may be appropriately combined to implement the functions of each unit.

The image acquisition unit 21 acquires the three-dimensional image V0 of the chest of the subject for placing the virtual stent from the image storage server 3. In a case in which the three-dimensional image V0 has already been stored in the storage 13, the image acquisition unit 21 may acquire the three-dimensional image V0 from the storage 13.

The extraction unit 22 extracts an aorta region as the blood vessel region from the three-dimensional image V0 using, for example, the method disclosed in JP2010-200925A and JP2010-220742A. In this method, first, the positions and main axis directions of a plurality of candidate points forming a core line of the aorta are calculated on the basis of the value of voxel data forming the three-dimensional image V0. Alternatively, the Hessian matrix for the three-dimensional image V0 is calculated and the eigenvalue of the calculated Hessian matrix is analyzed to calculate the positional information and main axis direction of a plurality of candidate points forming the core line of the aorta. Then, a feature amount indicating the blood vessel, particularly, the aortic characteristics, are calculated for voxel data around the candidate point and it is determined whether or not the voxel data indicates the aorta on the basis of the calculated feature amount. The determination based on the feature amount is performed on the basis of an evaluation function which has been acquired in advance by machine learning. In this way, the blood vessel region, that is, the aorta region and the core line thereof are extracted from the three-dimensional image V0. The core line may be extracted by extracting the blood vessel region first and performing a thinning process for the blood vessel region.

Figure 3:
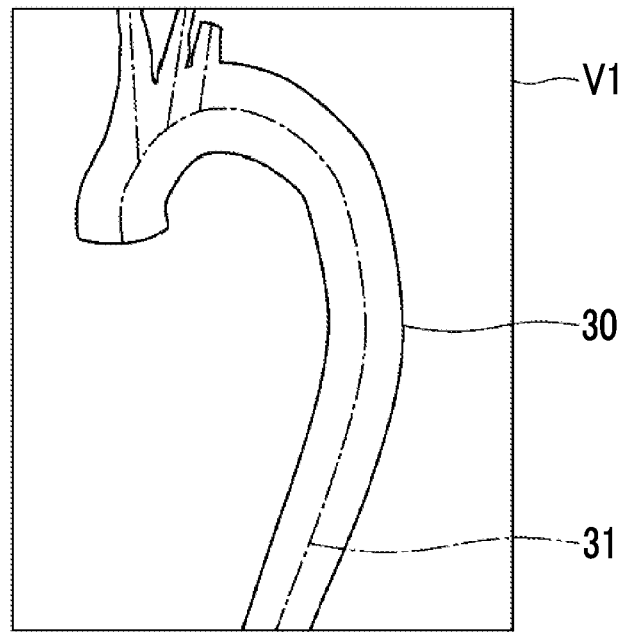
FIG. 3 is a diagram illustrating a three-dimensional image of a blood vessel region displayed on a display.

The display control unit 26 displays the extracted blood vessel region on the display 14. Since the extracted blood vessel region is a three-dimensional image, the display control unit 26 displays the three-dimensional image of the blood vessel region on the display 14 using a predetermined display method. Examples of the display method include projection methods, such as a maximum intensity projection (MIP) method and a minimum intensity projection (MinIP) method, and a volume rendering (VR) method. The three-dimensional image of the blood vessel region displayed on the display 14 is illustrated in FIG. 3. As illustrated in FIG. 3, a three-dimensional image V1 of a blood vessel region 30 is displayed on the display 14. A core line 31 of the blood vessel region 30 is also displayed in the three-dimensional image V1.

The information acquisition unit 23 acquires the information of the diameter of the virtual stent placed in the blood vessel region, the maximum contour length of the virtual stent, and the start position in a case in which the virtual stent is placed. In this embodiment, the diameter of the virtual stent is acquired in response to an input from the operator through the input unit 15. Further, the information acquisition unit 23 acquires the information of the maximum contour length of the virtual stent and the start position of the virtual stent input by the operator through the input unit 15 with reference to the three-dimensional image V1 of the blood vessel region displayed on the display 14. The information of the maximum contour length is acquired by receiving the input of the value of the maximum contour length by the operator through the input unit 15.

Figure 4:
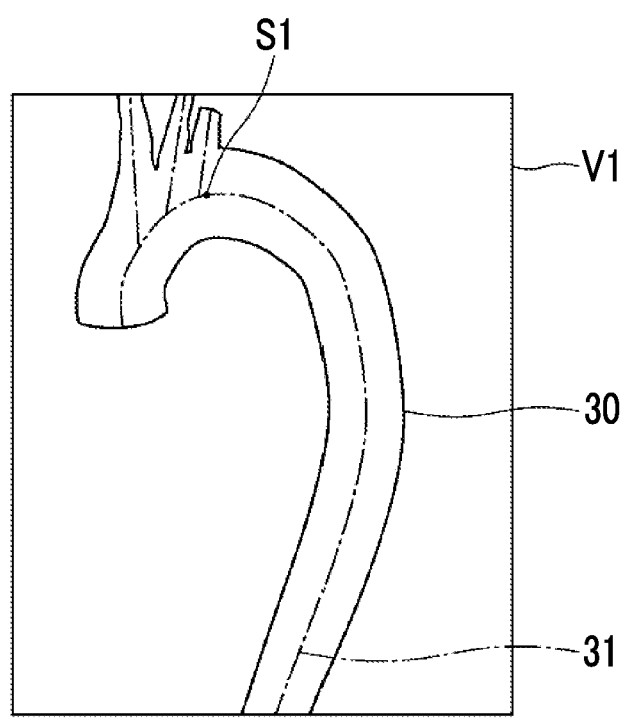
FIG. 4 is a diagram illustrating a three-dimensional image in which a start position of a virtual stent is designated.

FIG. 4 is a diagram illustrating the three-dimensional image V1 in which a start position S1 of the virtual stent is designated. In addition, after the start position S1 of the virtual stent is designated, the diameter of a cross section perpendicular to a core line 31 in the blood vessel region 30 in a predetermined range from the start position S1 may be measured to acquire the information of the diameter of the virtual stent. In addition, the area or perimeter of the cross section perpendicular to the core line 31 in the blood vessel region 30 in a predetermined range from the start position S1 may be measured and the information of the diameter of the virtual stent may be calculated from the measured area or perimeter. In a case in which the diameter of the blood vessel region 30 is measured, the measurement may be performed at only one position in a predetermined range from the start position S1 or may be performed at a plurality of positions. In a case in which the diameter is measured at a plurality of positions, a representative value, such as the average value or intermediate value of the diameters at the plurality of positions, may be used as the information of the diameter of the virtual stent. That is, the information acquisition unit 23 may estimate the diameter of the virtual stent from the blood vessel region.

Figure 5:
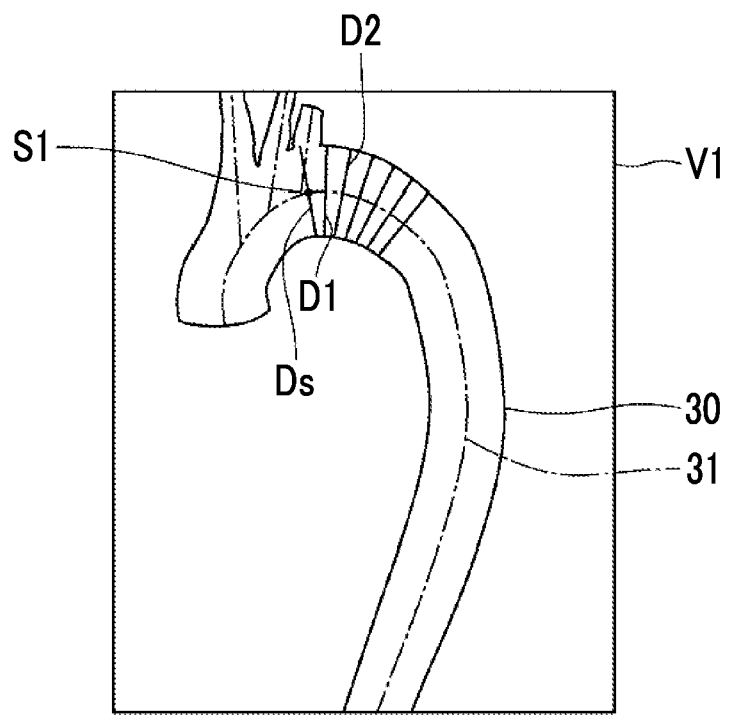
FIG. 5 is a diagram illustrating the setting of a maximum contour line of the blood vessel region.

The information acquisition unit 23 determines the maximum contour line of the blood vessel region 30 based on the start position S1 in order to place the virtual stent having the input maximum contour length. FIG. 5 is a diagram illustrating the determination of the maximum contour line. As illustrated in FIG. 5, first, the information acquisition unit 23 sets a cross section Ds perpendicular to the core line 31 at the start position S1. Then, a circle having the diameter of the virtual stent is defined in the cross section Ds and contour points of the circle are set on the circumference of the circle at predetermined intervals. Then, cross sections D1, D2, . . . are set at predetermined intervals along the core line in a predetermined range from the start position S1 to the end position. As in the cross section Ds, circles having the diameter of the virtual stent are defined in the cross sections D1, D2, . . . and contour points of the circles are set on the circumferences of the circles at predetermined intervals.

Figure 6:
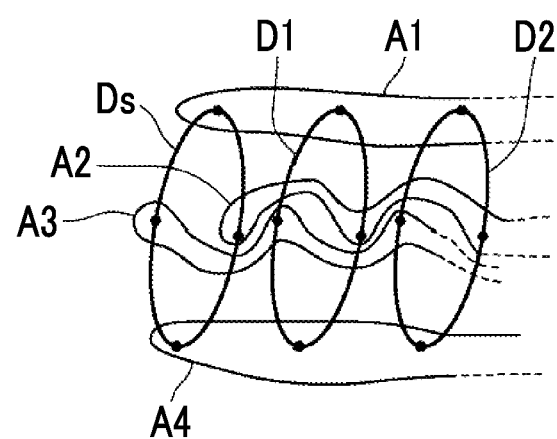
FIG. 6 is a diagram illustrating the setting of a contour point group.

Then, sets of the closest contour points between the contour points in the cross section Ds and the contour points in the cross section D1 adjacent to the cross section Ds are set. This is repeated in a predetermined range from the start position S1 to set contour point groups corresponding to each other on the circumferences corresponding to the cross sections perpendicular to the core line 31 as illustrated in FIG. 6. In FIG. 6, only the cross sections Ds, D1, and D2 are illustrated and the corresponding contour points among the contour points set in the cross sections Ds, D1, and D2 are surrounded by lines A1 to A4. Here, in FIG. 6, four contour points are set on the circumference. However, the invention is not limited thereto. It is preferable to set a larger number of contour points. Then, the information acquisition unit 23 connects the corresponding contour point groups to acquire the contour line groups of the blood vessel region 30 in a direction along the core line 31. In addition, among the acquired contour line groups, a contour line having the maximum length is determined as the maximum contour line. The side on which the maximum contour line exists in the blood vessel region 30, that is, the aorta is a large curvature side.

Figure 7:
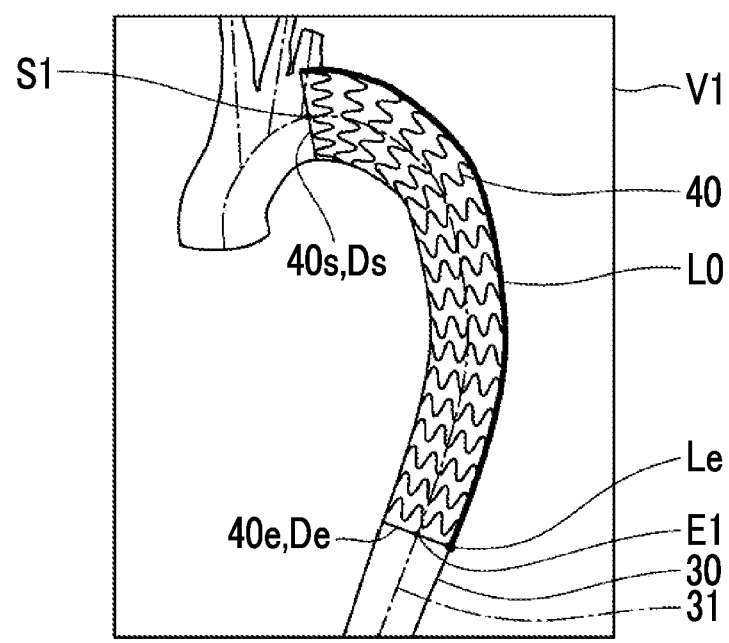
FIG. 7 is a diagram illustrating a three-dimensional image in which the virtual stent is placed.

The placement unit 24 places the virtual stent in the blood vessel region 30. The virtual stent to be placed has the diameter based on the information acquired by the information acquisition unit 23 and has the maximum contour length from the start position S1 along the maximum contour line of the blood vessel region 30. FIG. 7 is a diagram illustrating the three-dimensional image V1 in which a virtual stent 40 is placed. As illustrated in FIG. 7, in the three-dimensional image V1, the virtual stent 40 having a maximum contour length L0 from the start position S1 set on the core line 31 in the blood vessel region 30 along the maximum contour line is placed. In FIG. 7, a portion of the virtual stent 40 having the maximum contour length L0 is represented by a thick line. FIG. 7 also illustrates a mesh pattern forming the stent. An end position E1 of the virtual stent 40 on the core line 31 is set by placing the virtual stent 40 in this way. The end position E1 is an intersection point of the core line 31 and a cross section De of the blood vessel region 30 that passes through a position Le having the maximum contour length L0 on the maximum contour line of the virtual stent 40 and is perpendicular to the core line 31. As illustrated in FIG. 7, a stent cross section 40s of the virtual stent 40 at the start position S1 is matched with the cross section Ds perpendicular to the core line 31 at the start position S1. Further, a stent cross section 40e of the virtual stent 40 at the end position E1 is matched with the cross section De perpendicular to the core line 31 at the end position E1.

Here, in a case in which the stent is actually placed in the blood vessel, it is necessary to adjust the direction of the stent cross section so as not to block a branch of the blood vessel in the vicinity of both ends of the stent.

Figure 8:
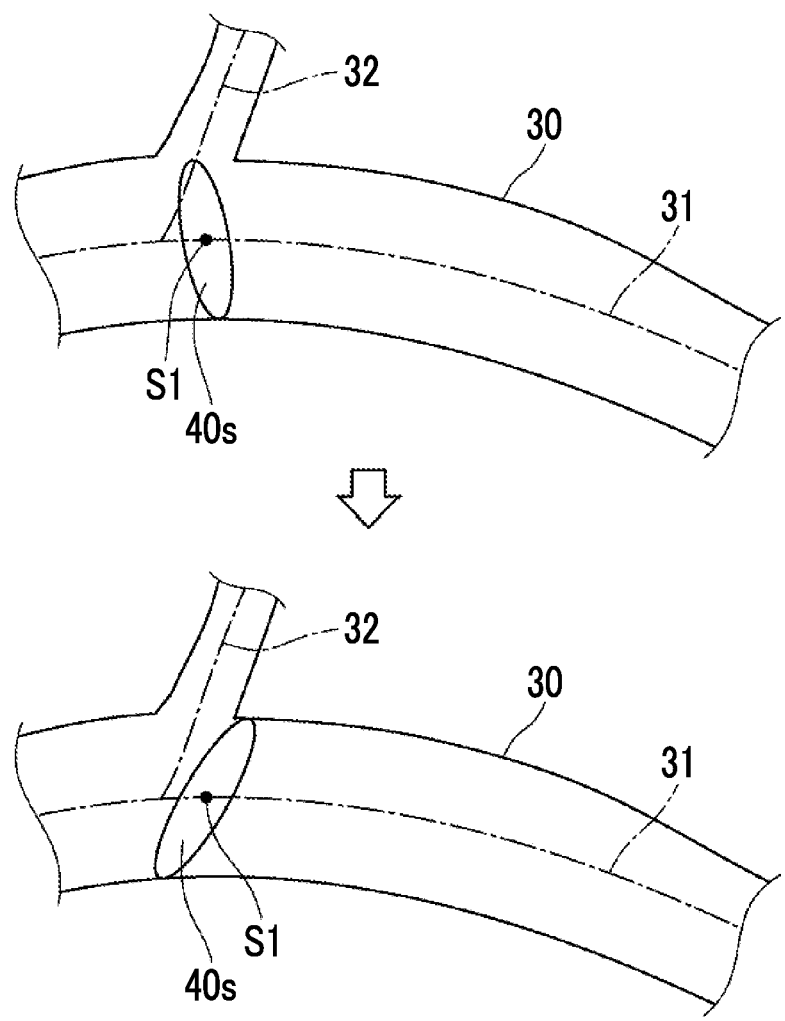
FIG. 8 is a diagram illustrating a change in the inclination of a cross section.

The inclination change unit 25 changes the inclination of the stent cross sections 40s and 40e which are the cross sections of the placed virtual stent 40 at the start position S1 and the end position E1 with respect to the cross sections Ds and De perpendicular to the core line 31. Specifically, the inclination change unit 25 changes the inclination of the stent cross sections 40s and 40e with respect to the cross sections Ds and De perpendicular to the core line 31 to avoid the overlap between the stent cross sections 40s and 40e and the branches of the blood vessel region 30. In order to avoid the overlap, the inclination change unit 25 determines whether or not each of the stent cross section 40s of the virtual stent 40 at the start position S1 and the stent cross section 40e of the virtual stent 40 at the end position E1 overlaps the branch of the blood vessel region 30. FIG. 8 is a diagram illustrating a change in the inclination of the cross section. In FIG. 8, the virtual stent 40 is not illustrated. In an example illustrating in the upper diagram of FIG. 8, the stent cross section 40s of the virtual stent at the start position S1 overlaps a branch of the blood vessel region 30. Here, the determination of whether or not the stent cross section 40s overlaps the branch may be performed by determining whether or not the stent cross section 40s overlaps a core line 32 branched from the core line 31.

In a case in which the stent cross section 40s overlaps the branch of the blood vessel region 30, the inclination change unit 25 changes the inclination of the stent cross section 40s. In this case, the inclination change unit 25 rotates the stent cross section 40s around an intersection point of the stent cross section 40s and the core line 31, that is, the start position S1 until the stent cross section 40s does not overlap the core line 32 along the maximum contour line of the blood vessel region 30. That is, the inclination change unit 25 brings the stent cross section 40s into contact with the contour line of the blood vessel region having the maximum contour length to change the inclination of the stent cross section 40s. As a result, the stent cross section 40s does not overlap the branch of the blood vessel region 30 as illustrated in the lower diagram of FIG. 8. Therefore, in the three-dimensional image V1, the stent cross section 40s at the start position S1 is not located at the branch as illustrated in FIG. 9.

Figure 9:
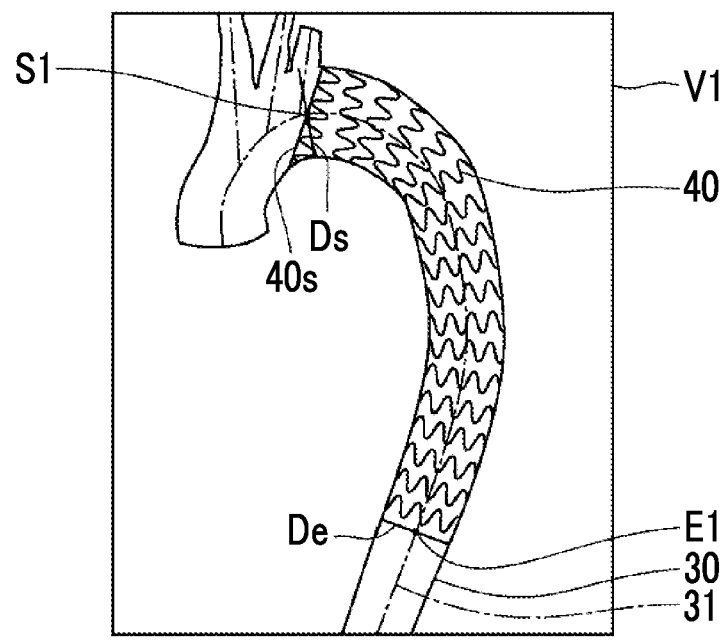
FIG. 9 is a diagram illustrating a state in which the inclination of a cross section is changed in the three-dimensional image in which the virtual stent is placed.
Figure 10:
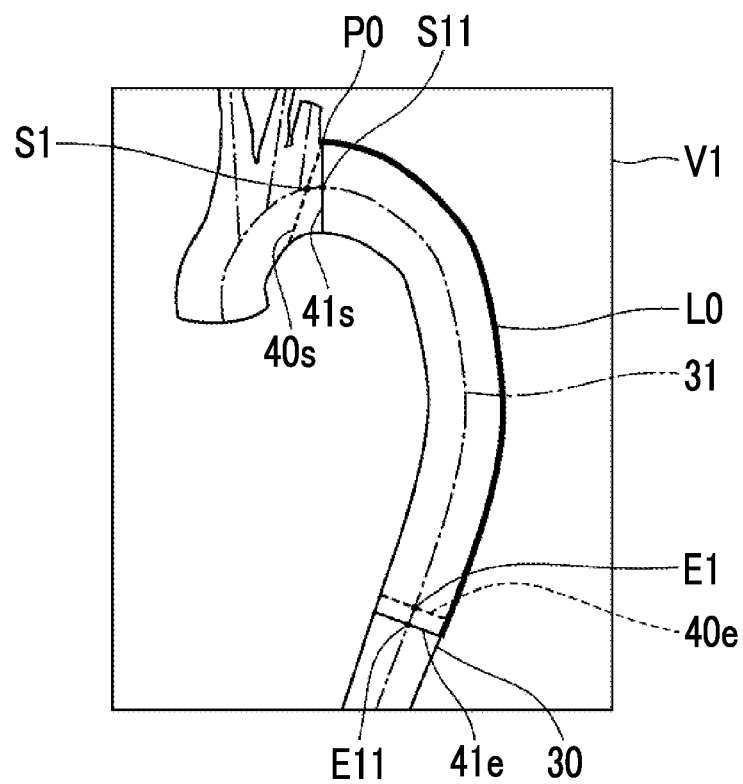
FIG. 10 is a diagram illustrating a change in the position where the virtual stent is placed.

In the state illustrated in FIG. 9, the virtual stent 40 does not have the maximum contour length L0 along the maximum contour line of the blood vessel region 30. Therefore, in a case in which the inclination of the stent cross section 40s of the virtual stent is changed to change the start position S1, the placement unit 24 changes the position where the virtual stent 40 is placed with the change in the inclination of the stent cross section 40s. FIG. 10 is a diagram illustrating a change in the position where the virtual stent is placed. In FIG. 10, the stent cross section 40s whose inclination has been changed as described above is represented by a dashed line. The placement unit 24 calculates an intersection point P0 between the stent cross section 40s whose inclination has been changed and the maximum contour line of the blood vessel region 30. Then, a cross section that passes through the intersection point P0 and is perpendicular to the core line 31 is set as a new stent cross section 41s of the virtual stent at the start position. The new stent cross section 41s intersects the core line 31 at a new start position S11. Furthermore, the placement unit 24 places the virtual stent 40 having the maximum contour length L0 in the blood vessel region 30 again along the maximum contour line from the intersection point P0. In this case, since the new start position S11 is shifted from the start position S1 in the direction along the blood vessel region 30, the end position of the virtual stent 40 having the maximum contour length L0 is also moved from the end position E1 to a new end position E11. A cross section perpendicular to the core line 31 at the new end position E11 is a new stent cross section 41e. In FIG. 10, the mesh pattern of the virtual stent is not illustrated for explanation.

The display control unit 26 displays the three-dimensional image V1 as described above or displays various kinds of information required for processes.

Figure 11:
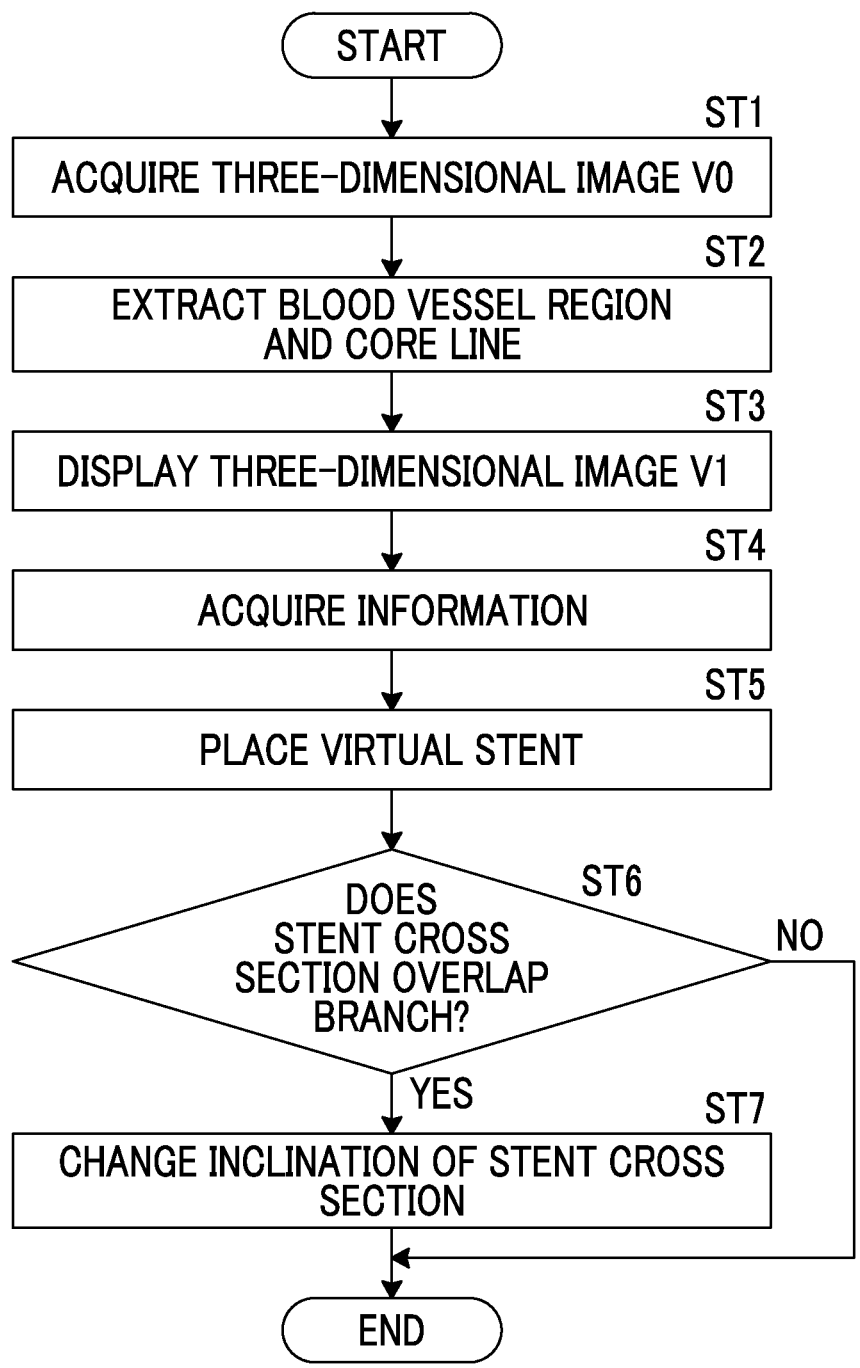
FIG. 11 is a flowchart illustrating a process performed in this embodiment.

Next, the process performed in this embodiment will be described. FIG. 11 is a flowchart illustrating the process performed in this embodiment. First, the image acquisition unit 21 acquires the three-dimensional image V0 (Step ST1). The extraction unit 22 extracts the blood vessel region 30 and the core line 31 of the blood vessel region 30 from the three-dimensional image V0 (Step ST2). In a case in which the core line 32 branched from the core line 31 is present in the three-dimensional image V0, the extraction unit 22 also extracts the core line 32. Then, the display control unit 26 displays the three-dimensional image V1 including the blood vessel region 30 and the core line 31 (Step ST3). The information acquisition unit 23 acquires the information of the diameter of the virtual stent placed in the blood vessel region 30, the maximum contour length of the virtual stent, and the start position S1 in a case in which the virtual stent is placed (information acquisition; Step ST4). The placement unit 24 places the virtual stent 40 in the blood vessel region 30 (Step ST5). The inclination change unit 25 determines whether or not the stent cross sections 40s and 40e of the virtual stent 40 at the start position S1 and the end position E1 overlap the branches of the blood vessel region 30 (Step ST6).

In a case in which the determination result in Step ST6 is "No", the process ends. In a case in which the determination result in Step ST6 is "Yes", the inclination change unit 25 changes the inclination of the stent cross section with respect to the cross section perpendicular to the core line 31 (Step ST7). Then, the process ends.

As such, in this embodiment, the information on the diameter of the virtual stent 40 placed in the blood vessel region 30, the maximum contour length of the virtual stent 40, and the start position S1 in a case in which the virtual stent 40 is placed is acquired. Then, the virtual stent 40 having the maximum contour length L0 from the start position S1 along the maximum contour line of the blood vessel region 30 is placed in the blood vessel region 30. Therefore, it is not necessary to repeat the placement of the stent and the setting of the maximum contour length until the stent with a desired size is determined. As a result, it is possible to simplify the operation of placing the virtual stent 40.

The inclination of the stent cross sections 40s and 40e of the virtual stent 40 placed in the blood vessel region 30 at the start position S1 and the end position E1 with respect to the cross sections Ds and De perpendicular to the core line 31 is changed. Therefore, the inclination of the stent cross sections 40s and 40e can be appropriately changed such that the virtual stent 40 does not block the branch of the blood vessel. As a result, in a case in which the stent is actually placed in the blood vessel, it is possible to prevent the stent from blocking the branch of the blood vessel with reference to the position where the virtual stent 40 is placed.

Figure 12:
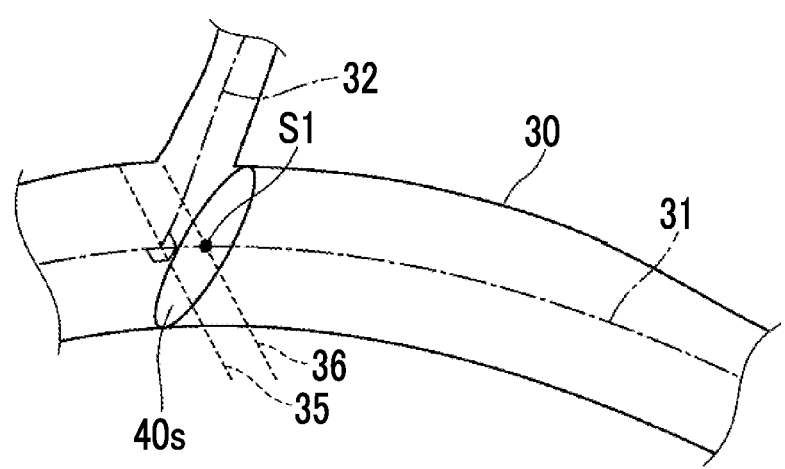
FIG. 12 is a diagram illustrating a change in the inclination of the cross section.

In the above-described embodiment, the inclination change unit 25 rotates the stent cross section 40s around the start position S1 along the maximum contour line of the blood vessel region 30. However, as illustrated in FIG. 12, an axis 35 perpendicular to both the core line 31 and the core line 32 may be set, an axis 36 that passes through the start position S1 and is parallel to the axis 35 may be set, and the stent cross section 40s may be rotated on the axis 36 as a rotation axis.

In the above-described embodiment, in a case in which the stent cross sections 40s and 40e overlap the branches of the blood vessel region 30, the inclination change unit 25 changes the inclination of the stent cross sections 40s and 40e until the stent cross section 40s does not overlap the core line 32. However, the inclination change unit 25 may change the inclination of the stent cross sections 40s and 40e in response to a command input by the operator through the input unit 15.

Figure 13:
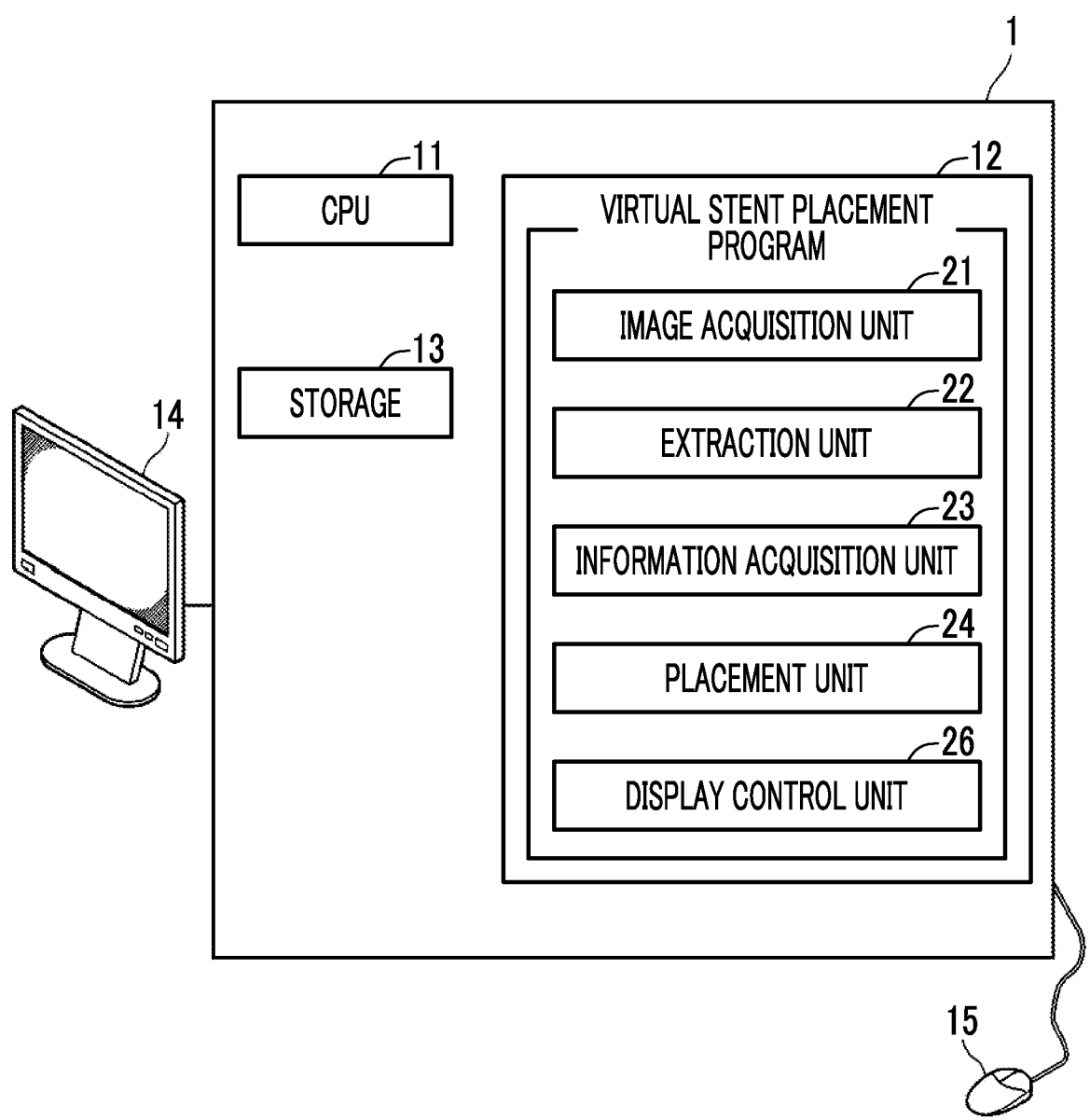
FIG. 13 is a diagram schematically illustrating the configuration of a virtual stent placement apparatus according to another embodiment of the invention.

In the above-described embodiment, the virtual stent placement apparatus 1 comprises the inclination change unit 25. However, as illustrated in FIG. 13, the inclination change unit 25 may be omitted. In this case, the operator may set and input the start position S1 and the maximum contour length L0 with the input unit 15 such that the stent cross sections 40s and 40e of the virtual stent 40 are not located at the branches of the blood vessel region 30 while observing the three-dimensional image V0 displayed on the display 14.

In the above-described embodiment, the extraction unit 22 extracts the blood vessel region 30 and the core line 31 from the three-dimensional image V0. However, the extraction unit 22 may extract only the blood vessel region 30. In a case in which the core line 31 is required in the process of the placement unit 24 and the inclination change unit 25, the placement unit 24 and the inclination change unit 25 may extract the core line 31.

In the above-described embodiment, the aorta is extracted as the blood vessel region 30 from the three-dimensional image V0. However, the blood vessel region 30 is not limited to the aorta as long as the stent needs to be placed in the blood vessel. For example, the coronary artery or the cerebral artery may be extracted as the blood vessel region 30.

In the above-described embodiment, the CT image is used as the medical image. However, the invention is not limited thereto. For example, an MRI image and a PET image may be used.

EXPLANATION OF REFERENCES

1: virtual stent placement apparatus
2: three-dimensional imaging apparatus
3: image storage server
4: network
11: CPU
12: memory
13: storage
14: display
15: input unit
21: image acquisition unit
22: extraction unit
23: information acquisition unit
24: placement unit
25: inclination change unit
26: display control unit
30: blood vessel region
31, 32: core line
35, 36: axis
40: virtual stent
40s, 40e: stent cross section
41s, 41e: new stent cross section
A1 to A4: line
Ds: cross section at start position
D1, D2: cross section
De: cross section at end position
E1: end position
E11: new end position
L0: maximum contour length Le: position where virtual stent has maximum contour length
S1: start position
S11: new start position
P0: intersection point
V0, V1: three-dimensional image

What is claimed is:

1. A virtual stent placement apparatus comprising:
a storage device for storing information comprising a medical image; and
a processor coupled to the storage device and configured at least to:
extract a blood vessel region from the medical image;
acquire information of a diameter of a virtual stent which is placed in the blood vessel region, a maximum contour length of the virtual stent, and a start position in a case in which the virtual stent is placed;
place the virtual stent having the maximum contour length from the start position along a maximum contour line of the blood vessel region in the blood vessel region;
extract a core line of the blood vessel region from the medical image; and
change an inclination of stent cross sections which are cross sections of the placed virtual stent at the start position and an end position with respect to cross sections perpendicular to the core line by changing the inclination of the stent cross section with respect to the cross section perpendicular to the core line to avoid an overlap between the stent cross section and a branch of the blood vessel region.

2. The virtual stent placement apparatus according to claim 1, wherein the processor is further configured to set an end position of the virtual stent on the basis of a position of the maximum contour length.

3. The virtual stent placement apparatus according to claim 2, wherein the processor is further configured to estimate the diameter of the virtual stent from the blood vessel region.

4. The virtual stent placement apparatus according to claim 1, wherein the processor is further configured to estimate the diameter of the virtual stent from the blood vessel region.

5. The virtual stent placement apparatus according to claim 1, wherein the processor is further configured to receive a command to change the inclination of the stent cross section and changes the inclination of the stent cross section with respect to the cross section perpendicular to the core line.

6. The virtual stent placement apparatus according to claim 1,
wherein the processor is further configured to bring the stent cross section into contact with a contour line of the blood vessel region having the maximum contour length to change the inclination of the stent cross section.

7. The virtual stent placement apparatus according to claim 1, wherein processor is further configured to change a position where the virtual stent is placed with the change in the inclination of the stent cross section.

8. A virtual stent placement method for a virtual stent placement apparatus comprising:
extracting a blood vessel region from a medical image;
acquiring information of a diameter of a virtual stent which is placed in the blood vessel region, a maximum contour length of the virtual stent, and a start position in a case in which the virtual stent is placed;
placing the virtual stent having the maximum contour length from the start position along a maximum contour line of the blood vessel region in the blood vessel region;
extracting a core line of the blood vessel region from the medical image; and
changing an inclination of stent cross sections which are cross sections of the placed virtual stent at the start position and an end position with respect to cross sections perpendicular to the core line by changing the inclination of the stent cross section with respect to the cross section perpendicular to the core line to avoid an overlap between the stent cross section and a branch of the blood vessel region.

9. A non-transitory computer readable medium storing a virtual stent placement program for a virtual stent placement apparatus comprising a processor, the virtual stent placement program configures the processor to perform functions comprising:
extracting a blood vessel region from a medical image;
acquiring information of a diameter of a virtual stent which is placed in the blood vessel region, a maximum contour length of the virtual stent, and a start position in a case in which the virtual stent is placed;
placing the virtual stent having the maximum contour length from the start position along a maximum contour line of the blood vessel region in the blood vessel region;
extracting a core line of the blood vessel region from the medical image; and
changing an inclination of stent cross sections which are cross sections of the placed virtual stent at the start position and an end position with respect to cross sections perpendicular to the core line by changing the inclination of the stent cross section with respect to the cross section perpendicular to the core line to avoid an overlap between the stent cross section and a branch of the blood vessel region.

* * * * *